United States Patent
Smedman et al.

(10) Patent No.: US 11,698,342 B2
(45) Date of Patent: Jul. 11, 2023

(54) METHOD AND SYSTEM FOR ANALYSING FLUOROSPOT ASSAYS

(71) Applicant: MABTECH PRODUCTION AB, Nacka Strad (SE)

(72) Inventors: Christian Smedman, Stockholm (SE); Joakim Jalden, Stollentuna (SE); Daniel Pelikan, Vange (SE); Pol Del Aguila Pla, Solna (SE); Klas Magnusson, Bandhagen (SE)

(73) Assignee: MABTECH AB, Nacka Strand (SE)

( * ) Notice: Subject to any disclaimer, the term of this patent is extended or adjusted under 35 U.S.C. 154(b) by 591 days.

(21) Appl. No.: 16/627,029

(22) PCT Filed: Jun. 27, 2018

(86) PCT No.: PCT/SE2018/050691
§ 371 (c)(1),
(2) Date: Dec. 27, 2019

(87) PCT Pub. No.: WO2019/004913
PCT Pub. Date: Jan. 3, 2019

(65) Prior Publication Data
US 2020/0116636 A1    Apr. 16, 2020

(30) Foreign Application Priority Data

Jun. 29, 2017  (SE) .................................. 1730177-1

(51) Int. Cl.
*G01N 21/64*      (2006.01)

(52) U.S. Cl.
CPC . *G01N 21/6428* (2013.01); *G01N 2021/6439* (2013.01); *G01N 2021/6471* (2013.01)

(58) Field of Classification Search
CPC ....... G01N 21/6428; G01N 2021/6439; G01N 2021/6471
See application file for complete search history.

(56) References Cited

U.S. PATENT DOCUMENTS

| | | | |
|---|---|---|---|
| 6,410,252 B1 | 6/2002 | Lehmann | |
| 2005/0220675 A1* | 10/2005 | Reed | ..................... B01L 3/5025 422/400 |

(Continued)

FOREIGN PATENT DOCUMENTS

| | | |
|---|---|---|
| EP | 2302363 A2 | 3/2011 |
| EP | 3081230 A1 | 10/2016 |
| WO | 2016149120 A1 | 9/2016 |

OTHER PUBLICATIONS

Oliver Rosin; International Search Report for International Patent Application No. PCT/SE2018/050691, dated Apr. 9, 2018, 3 pages.

(Continued)

*Primary Examiner* — Blake C Riddick

(57) ABSTRACT

Disclosed is a method for analysing FluoroSpot assays. The method comprises illuminating a well of an assay plate with at least one excitation light, capturing at least one image of the well, in raw image format, for each excitation light, generating a model of analyte release distribution in the well for each excitation light, and clustering a plurality of co-positioned fluorospots as a multiple secretion fluorospot, wherein the clustering is performed for all generated models, and wherein the clustering determines at least one multiple secretion fluorospot. The generation of the model of analyte release distribution for a given excitation light comprises deconvolving the captured at least one image of the well to estimate a pre-diffusion analyte distribution, and detecting potential analyte release sites based on local maxima therein.

13 Claims, 5 Drawing Sheets

(56) References Cited

U.S. PATENT DOCUMENTS

| | | | |
|---|---|---|---|
| 2011/0212853 A1* | 9/2011 | Cynis | G01N 33/6893 506/7 |
| 2011/0244477 A1* | 10/2011 | Dosenovic | G01N 33/6854 435/7.1 |
| 2012/0288850 A1* | 11/2012 | Soethout | G01N 33/56972 435/5 |
| 2013/0035246 A1* | 2/2013 | Gillis | G01N 33/5023 435/6.1 |
| 2014/0051586 A1* | 2/2014 | Pino | G01N 33/54306 506/18 |
| 2014/0295425 A1* | 10/2014 | Nagy | C12Q 1/6827 435/6.11 |
| 2015/0141491 A1* | 5/2015 | Nagy | A61K 31/436 435/7.1 |
| 2016/0091491 A1* | 3/2016 | Davis | G01N 33/56972 435/39 |
| 2016/0238827 A1 | 8/2016 | Shroff et al. | |
| 2017/0168048 A1 | 6/2017 | Szmacinski et al. | |

OTHER PUBLICATIONS

Oliver Rosin; Written Opinion for International Patent Application No. PCT/SE2018/050691, dated Apr. 9, 2018, 6 pages.

Sylvia Janetzki et al.: "Stepping up ELISpot: Multi-Level Analysis in FluoroSpot Assays", CELLS, vol. 3, No. 4, Nov. 27, 2014 (Nov. 27, 2014), pp. 1102-1115, XP055501398, DOI: 10.3390/cells3041102 chapter 3; abstract; figure 6 chapter 2.

Janetzki et al. Cells 3:1102-1115 (2014).

Gazagne et al. J. Immunological Methods 283: 91-98 (2003).

Dillenbeck et al. Cells 3:1116-1130 doi:10.3390/cells3041116.

Rehbahn et al, Computer Methods and Programs in Biomedicine 92:54-65 (2008).

Karulin et al. Handbook of ELISPOT: Methods and Protocols Methods in Molecular Biology 792:125-143 Chapter 11 (2012) Springer Science+Business Media.

Lakos et al. J. of Immunological Methods 433 17-22 (2016).

Beck and Teboulle, SIAM J. Imaging Sciences 2(1):183-202 (2009).

Geman et al., IEEE Transactions on pattern analysis and machine intelligence 14(3):367-383 (1992).

Parikh, Neal, and Boyd, Stephen, Proximal Algorithms, Foundations and trends in Optimization 1(3);123-231 (2013).

Boyd et al, Distributed Optimization and Statistical Learning via the alternating Direction Method of Multipliers, in Foundations and Tends in Machine Learning 3(1), Chapter 3 (2010).

Chen et al., Alternating Direction Method of Multipliers for Nonlinear Image Restoration Problems, in IEEE Transactions on Image Processing, vol. 24, No. 1, pp. 33-43, Jan. 2015.

M. Tao, J. Yang. Alternating direction algorithms for total variation deconvolution in image reconstruction. Optimization Online. 2009 .http://www.optimization-online.org/DB_FILE/2009/11/2463.pdf.

Rebhahn et al., published "Automated analysis of two- and three-color fluorescent Elispot (Fluorospot) assays for cytokine secretion" in Computer methods and programs in Biomedicine, 2008, vol. 92, pp. 54-65.

Dupé et al., published "Deconvolution of Confocal Microscopy Images Using Proximal Iteration and Sparse Representations" in Part of Proceedings of the 5th IEEE International Symposium on Biomedical Imaging: From Nano to Macro (ISBI), May 14-17, 2008, Paris, France.

Dupé et al., published "A Proximal Iteration for Deconvolving Poisson Noisy Images Using Sparse Representations" in IEEE Transactions on Image Processing, vol. 18, No. 2, in Feb. 2009, pp. 310-321.

Bromage E. et al published "The third dimension of ELISPOTs: Quantifying antibody secretion from individual plasma cells" in Journal of Immunological Methods, vol. 346, on May 22, 2009, pp. 75-79.

Gilles et al., published DiAna, an ImageJ tool for object-based 3D co-localization and distance analysis, in Methods on Nov. 24, 2016, vol. 115, pp. 55-64.

Cui et al., published "Self-adjusting Nuclei Segmentation (SANS) of Hematoxylin-Eosin Stained Histopathological Breast Cancer Images" in IEEE International Conference on Bioinfomnatics and Biomedicine (BIBM) on Dec. 15-16, 2016 in Shenzhen, China, pp. 956-963.

Swedish Search Report and Technical Office Action issued in SE Patent Application. SE1730177-1 dated Mar. 16, 2018, 3 pages.

Pla et al., published "Cell Detection on Image-Based Immunoassays" in IEEE 15th International Symposium on Biomedical Imaging, on Apr. 4-7, 2018 in Washington, D.C., USA.

Pla et al., published "Cell Detection by Functional Inverse Diffusion and Non-negative Group Sparsity—Part I: Modeling and Inverse Problems" in IEEE Transactions on Signal Processing, vol. 66, No. 20, on Oct. 15, 2018, pp. 5407-5421.

Pla et al., published "Cell Detection by Functional Inverse Diffusion and Non-negative Group Sparsity—Part II: Proximal Optimization and Performance Evaluation" in IEEE Transactions on Signal Processing, vol. 66, No. 20, on Oct. 20, 2018, pp. 5422-5437.

Technical Office Action issued in SE Patent Application. SE1730177-1 dated Mar. 29, 2019, 10 pages.

Technical Office Action issued in SE Patent Application. SE1730177-1 dated Sep. 13, 2019, 07 pages.

Introduction to the AID EliSpot/FiuoroSpot Reader Systems AID EliSpot Software Version 7.x [online], AID Autoimmun Diagnostika GmbH, Retrieved from the Internet:http://sydney.edu.au/medicine/bosch/facilities/molecularbiology/UserGuide_V7.pdf; 2011, pp. 1-73.

Lehmann, Paul V., et al., Chapter 11: How ELISPOT Morpholoty Reflects on the Productivity and Kinetics of Cells' Secretory Activity, Handbook of ELISPOT Methods and Protocols, Second Edition, 2016, pp. 125-143.

* cited by examiner

METHOD AND SYSTEM FOR ANALYSING FLUOROSPOT ASSAYS

TECHNICAL FIELD

The present disclosure relates generally to investigative techniques such as assays; and more specifically, to methods and systems for analysing fluorospot assays. The present disclosure also relates to a computer implementable program operable to execute the aforesaid method on the aforesaid apparatus.

BACKGROUND

Typically, investigative procedures, such as assays, are employed in fields of medicine, molecular biology, and so forth. For example, assays are widely utilized in immunology for determining rate of activation of cells in response to vaccines, infections, allergens, etc. Assays involving antibodies as key components are typically referred to as immunoassays. Examples of immunoassays include, but are not limited to, Enzyme-Linked Immunosorbent Assay (ELISA), Enzyme-Linked ImmunoSpot (ELISPOT) assay, fluorospot assay.

Generally, the immunoassays include detection and quantitation of analytes in liquid samples or the monitoring of secreted analytes (for example, cytokines and immunoglobulins) by cells under observation. For example, in a fluorospot assay, cytokine-specific capture antibodies may be added to an assay plate having wells therein. Thereafter, cells may be added to the wells in presence or absence of activating stimuli and the assay plate may be incubated to allow for cytokine secretion by the cells. The secreted cytokines may be captured by the immobilized cytokine-specific capture antibodies at the bottom of wells. Thereafter, the cells may be removed and the wells may be washed and added with cytokine-specific detection antibodies and fluorophore conjugates. Finally, secretory footprints (or spots) of the secreted cytokines are captured by way of imaging, and such images are analysed for identifying multiple analytes, counting number of cells secreting the analytes, and the like.

However, there exist a number of limitations associated with analysis of such assays. Firstly, the cells under observation secrete the analytes in different quantities, thereby creating spots of varying sizes and intensities. Therefore, over a period of time, such secretion may lead to different spatial intensity profiles among spots of the analytes. Further, in many instances, the captured images may be saturated (or over exposed) by imaging equipment, and the true spatial intensity profiles of the spots are not clearly visible. Often, the cells are closely located to each other, thereby, leading to overlap of the spots in the captured images. Currently existing analytic techniques are not sufficiently developed to accurately determine secretion intensities of individual cells, and distinguish individual spots. The saturation of captured images further exacerbates problems associated with distinguishing individual spots from overlapped spots. Secondly, the currently existing techniques are unable to accurately determine centres of the spots. Specifically, the centres of spots emit stronger fluorescent signals as compared to other regions of the spots, thereby, facilitating identification of multiple secretions from a single cell. However, due to existing limitations in accurate determination of the centres of spots, identification of multiple secretions from the cells is difficult, and prone to errors. Thirdly, equipment employed for currently existing techniques introduces problems in the analysis of assays, such as compression of the captured images by the imaging equipment, inaccurate capture of images (such as shift between the images), blurring in the captured images on account of vibrations in the equipment, chromatic aberration and so forth.

Fourthly, the equipment employed for conventional techniques fail to effectively measure the concentration of analytes in one or more wells of the array. Furthermore, it deploys duplication of tests for measuring the concentration of the analytes, thereby, increasing time, cost and complexity of the process. Nonetheless, the entire process results in a reduction of efficacy in determining the potential analyte releasing cells and the concentration of the analyte in the well.

Therefore, in light of the foregoing discussion, there exists a need to overcome the aforementioned drawbacks associated with analysis of assays.

SUMMARY

The present disclosure seeks to provide a method for analysing fluorospot assays. The present disclosure also seeks to provide a system for analysing fluorospot assays. The present disclosure seeks to provide a solution to the existing problems of inaccurate determination of secretion intensities of individual cells, errors in distinguishing individual spots and measuring concentration of the analytes in conventional assay analysis techniques. An aim of the present disclosure is to provide a solution that overcomes at least partially the problems encountered in prior art, and provides an efficient, robust, and easy to implement assay analysis technique.

In a first aspect, an embodiment of the present disclosure provides a method for analysing fluorospot assays, the method comprising:
  (i) illuminating a well of an assay plate having plurality of wells, with a plurality of excitation lights, wherein at a given time, the well of the assay plate is illuminated by only one excitation light;
  (ii) capturing at least one image of the well, in raw image format, for each of the at least one excitation light;
  (iii) generating a model of analyte release distribution in the well for each of the at least one excitation light, wherein the generation of the model of analyte release distribution in the well for a given excitation
    (a) deconvolving the captured at least one image of the well for the given excitation light to estimate a pre-diffusion analyte distribution; and
    (b) detecting at least one potential analyte release site based on local maxima in the pre-diffusion analyte distribution; and
  (iv) for the plurality of excitation lights employed to illuminate the well of the assay plate, clustering a plurality of co-positioned fluorospots as a multiple secretion fluorospot, wherein the clustering is performed for all generated models of analyte release distribution, and wherein the clustering determines at least one multiple secretion fluorospot,
characterized in that the method includes:
generating the model of analyte release distribution in the well for each of the plurality of excitation light comprises optimizing the pre-diffusion analyte distribution based on the detected at least one potential release site; and modifying the model of analyte release distribution in the well to analyse at least one fluorospot therein, wherein optimizing the pre-diffusion analyte distribution, based on the detected at least one potential analyte release site, is implemented iteratively at least once, and comprises employing at least one of: alternating direction methods, multiplicative update rules, forward-backward proximal gradient algorithms.

The present disclosure is of advantage in that it efficiently detects and quantitates the analytes secreted by the cells in liquid samples.

Embodiments of the disclosure are advantageous in terms of providing a method that conforms to an advanced and highly efficient and robust analytical technique. Moreover, the embodiments of the disclosure are advantageous in terms of an automatic sensing mechanism for detecting the high fluorescent intensity and correlating the fluorescent intensity with the concentration of the analyte in the well(s). Beneficially, the analyte distribution and/or concentration measurement require minimal or no manual intervention, thereby reducing the cost of operation of the assay.

Optionally, the plurality of excitation lights for illuminating the well of the assay plate depends on the at least one fluorophore-detected analyte in the spatially defined area of the well.

Optionally, deconvolving the captured at least one image of the well comprises implementing at least one of: sparsity-promoting regularization, multiplicative update rules, forward-backward proximal gradient algorithms.

Optionally, modifying the model of analyte release distribution in the well is based on at least one user-selectable parameter, wherein the at least one parameter is selected from a group comprising: fluorospot/fluorescent intensity, fluorospot size, estimated amount of analyte release, fluorospot colour, area of interest in the well.

Optionally, clustering the plurality of co-positioned fluorospots employs a distance-based hierarchical clustering algorithm.

Optionally, the method further comprises displaying a resultant model of analyte release distribution in the well, wherein the model of analyte release distribution, based on the detected at least one potential analyte release site, is implemented iteratively at least once, and comprises employing at least one of: alternating direction methods, multiplicative update rules, forward-backward proximal gradient algorithms, wherein the resultant model comprises the detected at least one fluorospot, and wherein single secretion fluorospots and multiple secretion fluorospots are represented.

In a second aspect, an embodiment of the present disclosure provides a system for analysing fluorospot assays, the system comprising:
(i) a light source arrangement configured to generate a plurality of excitation lights, wherein at a given time, the light source arrangement generates only one excitation light;
(ii) a collimation arrangement positioned on an optical path of a generated excitation light, wherein the collimation arrangement is configured to collimate the generated excitation light;
(iii) a multiband beam splitter positioned on an optical path of the collimated excitation light, the multiband beam splitter being supported by a support arrangement, wherein the multiband beam splitter is configured to
(a) reflect the collimated excitation light onto an assay plate for illuminating a well of the assay plate having a plurality of wells;
(b) receive a reflection of the excitation light and an emitted light from the assay plate; and
(c) reflect a portion of the reflected excitation light whilst transmitting a remaining portion of the reflected excitation light and the emitted light to a filtering arrangement;
(iv) the filtering arrangement comprising a filter wheel and at least one emission filter, wherein the filter wheel is configured to accommodate the at least one emission filter therein, and wherein the at least one emission filter is configured to
(d) remove the remaining portion of the reflected excitation light received from the multiband beam splitter; and
(e) filter the emitted light whilst transmitting the emitted light to an optic arrangement;
(v) the optical arrangement configured to direct the filtered emitted light onto an imaging device;
(vi) the imaging device configured to capture at least one image of the well, in raw image format, for each of the plurality of excitation lights; and
(vii) a processing module coupled to the imaging device, wherein the processing module is configured to
(f) generate a model of analyte release distribution in the well for each of the plurality of excitation lights, wherein optimizing the pre-diffusion analyte distribution, based on the detected at least one potential analyte release site, is implemented iteratively at least once, and comprises employing at least one of: alternating direction methods, multiplicative update rules, forward-backward proximal gradient algorithms; and
(g) for the plurality of excitation lights employed to illuminate the well of the assay plate, cluster a plurality of co-positioned fluorospots as a multiple secretion fluorospot, wherein the clustering is performed for all generated models of analyte release distribution, and wherein the clustering determines at least one multiple secretion fluorospot.

Optionally, the system further comprises at least one excitation filter positioned on an optical path of the collimated excitation light, and wherein the at least one excitation filter is configured to filter the collimated excitation light.

Optionally, the light source arrangement comprises at least one light source positioned on an actuator arrangement, wherein the at least one light source is implemented by way of at least one of: Light Emitting Diode, halogen light source, xenon light source, laser light source.

Optionally, the multiband beam splitter is implemented by way of at least one of: a transparent mirror, a semitransparent mirror, a prism, a dichroic mirror.

Optionally, the optical arrangement comprises at least one of: telecentric lens, macro lens.

Optionally, the support arrangement is a filter cube.

Optionally, the system further comprises a visualization module coupled to the imaging device and the processing module, wherein the visualization module comprises a user interface rendered on a computing device associated with a user, and wherein the visualization module is configured to perform at least of: display the captured at least one image for each of the at least one excitation light, display the generated model of analyte release distribution in the well for each of the at least one excitation light, receive user input to control operation of the processing module, display a resultant model of analyte release distribution in the well.

Embodiments of the present disclosure substantially eliminate or at least partially address the aforementioned problems in the prior art, and enables accurate and reliable assay analysis.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

A better understanding of the present invention may be obtained through the following examples which are set forth to illustrate, but are not to be construed as limiting the present invention.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those in the art will understand that the drawings are not to scale. Wherever possible, like elements have been indicated by identical numbers.

Embodiments of the present disclosure will now be described, by way of example only, with reference to the following diagrams wherein.

Figure 1:
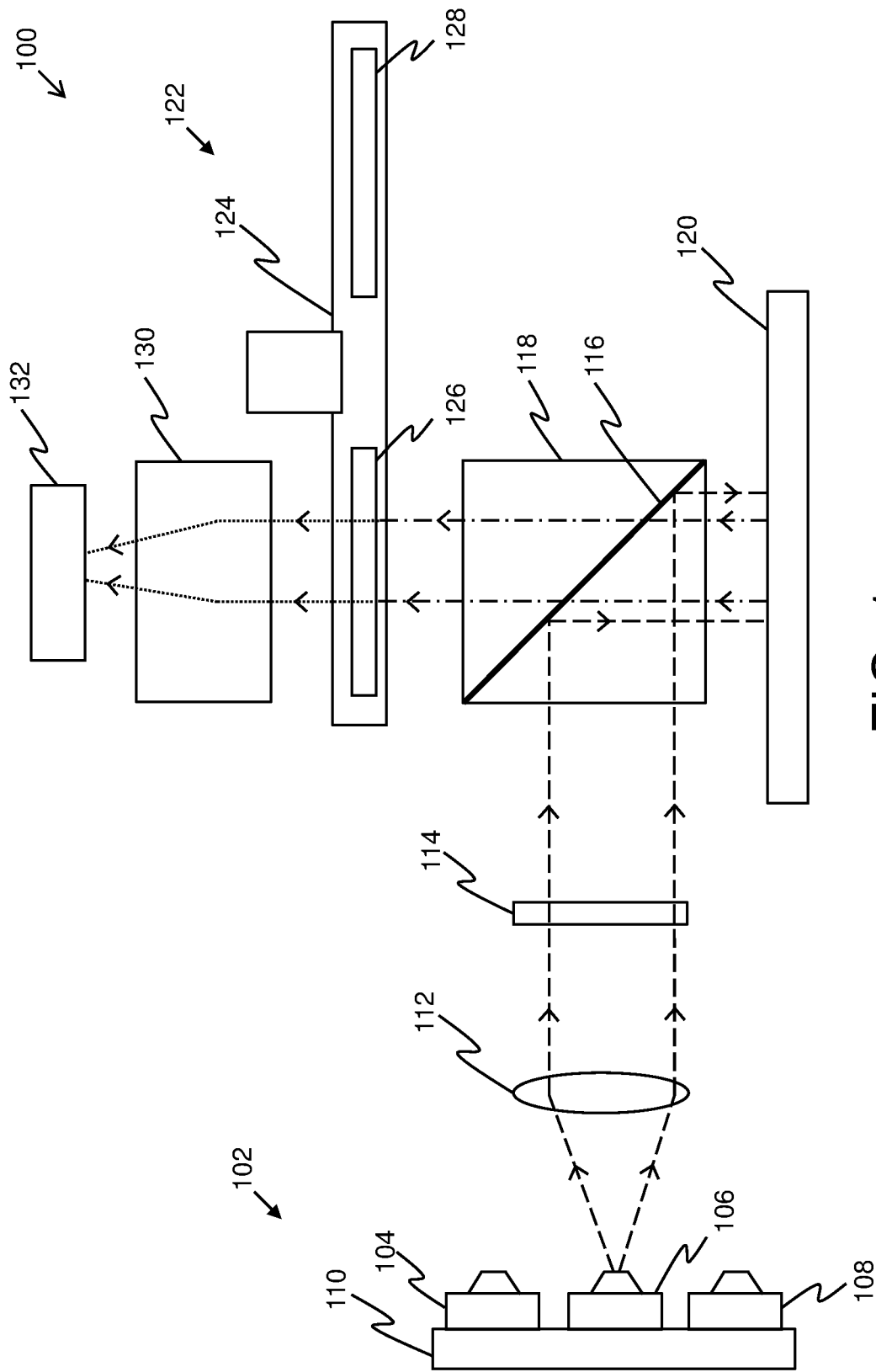
FIG. 1 is a schematic illustration of a system for analysing FluoroSpot assays, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

It is appreciated that certain features of the invention, which are for clarity described in the context of separate embodiments, may also be provided in combination in a single embodiment. Conversely various features of the invention, which are for brevity, described in the context of a single embodiment, may also be provided separately and/or in any suitable sub-combination.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

In one aspect, an embodiment of the present disclosure provides a method for analysing fluorospot assays, the method comprising:

(i) illuminating a well of an assay plate having plurality of wells, with a plurality of excitation lights, wherein at a given time, the well of the assay plate is illuminated by only one excitation light;

(ii) capturing at least one image of the well, in raw image format, for each of the at least one excitation light;

(iii) generating a model of analyte release distribution in the well for each of the at least one excitation light, wherein the generation of the model of analyte release distribution in the well for a given excitation (a) deconvolving the captured at least one image of the well for the given excitation light to estimate a pre-diffusion analyte distribution; and (b) detecting at least one potential analyte release site based on local maxima in the pre-diffusion analyte distribution; and (iv) for the plurality of excitation lights employed to illuminate the well of the assay plate, clustering a plurality of co-positioned fluorospots as a multiple secretion fluorospot, wherein the clustering is performed for all generated models of analyte release distribution, and wherein the clustering determines at least one multiple secretion fluorospot, characterized in that the method includes:

generating the model of analyte release distribution in the well for each of the plurality of excitation lights comprises optimizing the pre-diffusion analyte distribution based on the detected at least one potential release site; and modifying the model of analyte release distribution in the well to analyse at least one fluorospot therein.

In another aspect, an embodiment of the present disclosure provides a system for analysing fluorospot assays, the system comprising:

(i) a light source arrangement configured to generate at least one excitation light, wherein at a given time, the light source arrangement generates only one excitation light;

(ii) a collimation arrangement positioned on an optical path of a generated excitation light, wherein the collimation arrangement is configured to collimate the generated excitation light;

(iii) a multiband beam splitter positioned on an optical path of the collimated excitation light, the multiband beam splitter being supported by a support arrangement, wherein the multiband beam splitter is configured to (a) reflect the collimated excitation light onto an assay plate for illuminating a well of the assay plate having a plurality of wells;

(b) receive a reflection of the excitation light and an emitted light from the assay plate; and (c) reflect a portion of the reflected excitation light whilst transmitting a remaining portion of the reflected excitation light and the emitted light to a filtering arrangement;

(iv) the filtering arrangement comprising a filter wheel and at least one emission filter, wherein the filter wheel is configured to accommodate the at least one emission filter therein, and wherein the at least one emission filter is configured to
  (d) remove the remaining portion of the reflected excitation light received from the multiband beam splitter; and
  (e) filter the emitted light whilst transmitting the emitted light to an optic arrangement;
(v) the optical arrangement configured to direct the filtered emitted light onto an imaging device;
(vi) the imaging device configured to capture at least one image of the well, in raw image format, for each of the at least one excitation light; and
(vii) a processing module coupled to the imaging device, wherein the processing module is configured to
  (f) generate a model of analyte release distribution in the well for each of the at least one excitation light; and
  (g) cluster a plurality of co-positioned fluorospots as a multiple secretion fluorospot, wherein the clustering is performed for all generated models of analyte release distribution, and wherein the clustering determines at least one multiple secretion fluorospot.

The present disclosure provides a method and a system for analysing fluorescent assays. The described method and system are simple, robust, and easy to implement as compared to conventional techniques and equipment for analysis of assays. Beneficially, the described method accurately determines secretion intensities of cells by analysing different spatial intensity profiles among spots of the secreted analytes, and distinguishes individual spots. Further, the described method accurately determines centres of the spots, thereby, facilitating accurate identification of multiple secretions from a single cell. Furthermore, the method minimizes the risk of saturation of sensors by employing lower exposure to strong spots with high fluorescent intensities. Additionally, the system effectively measures the concentration of the analytes using a fully-automated sensor and calibration instrument. Moreover, the system described herein is inexpensive, easy to use, reliable, time efficient and reduces errors on account of manual inspection, compression of captured images by imaging equipment, blurring in the captured images, due to moving or vibrating components and/or imprecision in focus, wrong calibration, temporal or inherent noise and so forth.

In an embodiment, the term 'assay' used herein relates to fluorescence-based assays. Specifically, such fluorescence-based assays (for example, fluorospot assays) utilize principles of fluorescence in order to investigate cells, such as human cells, animal cells, and so forth. More specifically, the fluorescence-based assays enable simultaneous analysis of different analytes secreted by the cells under investigation, by employing fluorophore-labeled detection reagents to distinctly identify the different analytes. Therefore, secretory footprints (or fluorospots) of the different analytes are distinct from each other. Furthermore, fluorescence-based assays enable measuring the concentration of the analytes secreted by cells based on the fluorescent intensity of the analytes in a sample, specifically a liquid solution. According to an embodiment of the present disclosure, the term 'analyte' used herein relates to a substance that is analysed by implementing assays, such as a flurospot assay.

In an embodiment of the present disclosure, the term 'fluorospot assay' used herein relates to immunoassays, enumerating analytes secreted by cells. Specifically, the fluorospot assay relates to a method of detection of analytes secreted by cells, such as human cells, animal cells and so forth. Furthermore, in an embodiment, the term 'fluorospot' used herein relates to secretory footprints of an analyte. Specifically, the secretory footprint of an analyte is sensitive to a wavelength of an excitation light. More specifically, the secretory footprint of the analyte is captured by an imaging device for detection of the analyte.

The method for analysing fluorospot assays comprises illuminating a well of an assay plate having plurality of wells, with at least one excitation light, wherein at a given time, the well of the assay plate is illuminated by only one excitation light. Specifically, the plurality of wells of the assay plate (commonly referred to as a microtiter plate, microplate, microwell plate, and the like) include at least one fluorophore-detected analyte (hereinafter referred to as 'at least one analyte'). Further, upon illumination by the at least one excitation light, the at least one analyte may emit fluorescence (known as 'at least one emitted light'). Furthermore, at least one analyte secreted by the cell may be bound to a mixture of tag-labelled and biotinylated analyte-specific detection antibodies. Moreover, the mixture may be further bound to detection reagents conjugated to different fluorophores. In an embodiment, a wavelength of the at least one emitted light may be greater than a wavelength of the at least one excitation light. It is to be understood that although the method described herein relates to analysis of one well of the assay plate, the method may be implemented to analyse more than one well of the assay plate.

In an embodiment, the plurality of excitation lights for illuminating the well of the assay plate depends on the at least one fluorophore-detected analyte in the spatially defined area of the well. Since analytes may be detected using distinct fluorophore detection, a distinct excitation light may be employed to illuminate and analyse a distinct analyte. For example, a well of an assay plate including two fluorophore-detected cytokines 'A' and 'B' may be illuminated with two excitation lights 'L1' and 'L2'. In such example, wavelength of excitation light L1 may match wavelength of a fluorophore employed to label the cytokine A, and wavelength of excitation light L2 may match wavelength of a fluorophore employed to label the cytokine B.

Further, the method comprises capturing at least one image of the well, in raw image format, for each of the at least one excitation light. Specifically, the captured at least one image may be constituted using the at least one emitted light that is emitted from the at least one analyte when the well is illuminated by the at least one excitation light. More specifically, for a given excitation light, the captured at least one image corresponding thereto, visually represent secretory footprints (or fluorospots) of an analyte that is sensitive to wavelength of the given excitation light. It is to be understood, that a number (or a count) of the captured at least one image for different excitation lights may or may not be equal. Referring to the aforementioned example, 20 images of the well may be captured for the excitation light L1, and 30 images of the well may be captured for the excitation light L2. Therefore, the captured 20 images visually represent fluorospots of the cytokine A, and the captured 30 images visually represent fluorospots of the cytokine B.

According to an embodiment of the present disclosure, the at least one image of the well is indicative of spatially located analyte sources and temporal distribution. Specifically, the term 'spatially located analyte sources' relates to a spatial distribution of the fluorospots of the at least one analyte in an image of the well. Further, the term 'temporal distribution' relates to fluorospots of the at least one analyte at a certain time in the captured at least one image of the well. Specifically, the captured at least one image represents temporal distribution in the fluorospots of the at least one analyte. In an example, the captured at least one image of the well may provide an indication of the temporal distribution of an analyte based on the spatial distribution of the analyte and dispersion of the analyte in the well. In another example, the captured at least one image of the well may not comprise analyte in the well, and is captured for determining all well coordinates, depth of well, centre of well and the exact position of the well borders.

It will be appreciated that the captured at least one image of the well for each of the plurality of excitation lights are in raw image format. Beneficially, images captured in raw image format are in unprocessed form and are therefore free from colourspace-dependent encoding. Optionally, the captured at least one image of the well for each of the plurality of excitation lights have image file formats, including, but not limited to, Joint Photographic Experts Group format, Tagged Image File Format, Portable Network Graphics format, and Graphics Interchange Format.

Furthermore, capturing at least one image of the well is performed by way of imaging. Specifically, the term 'imaging' relates to representation or creation of an object (or a scene) by recording light (or other electromagnetic radiations) emanating from the object, by means of emission or reflection. More Specifically, a real image is produced on an image-sensing surface inside an imaging device during a timed exposure. Typically, the image-sensing surface comprises an array of pixels arranged in color-filter units (or cells) for generating red, blue, green and white image signals.

It will be appreciated that imaging is performed by using any one of: a high-dynamic-range imaging device, a low-dynamic-range imaging device, a digital camera. Embodiments of the disclosure employ a high-dynamic-range (indicated by 'HDR' hereafter) imaging device. Specifically, the HDR imaging employs combining two or more images to produce a greater range of luminance in a final image as compared to standard digital imaging techniques. More specifically, HDR imaging employs taking several images with different exposures and then merging the images into a single HDR image. In an example, the different exposures may be −1 EV, 0 EV and +1 EV. Beneficially, HDR imaging employs a suitable HDR software that enables high sensitivity, excellent measuring range, higher luminance, minimized risk of saturation of sensor, tone mapping, much greater range of colors and brightness, image alignment, filtering random noise, and so forth.

Further, the method comprises generating a model of analyte release distribution in the well for each of the at least one excitation light, wherein the generation of the model of analyte release distribution in the well for a given excitation light comprises deconvolving the captured at least one image of the well for the given excitation light to estimate a pre-diffusion analyte distribution, wherein such deconvolution is performed prior to local diffusion of at least one analyte, and detecting at least one potential analyte release site based on local maxima in the pre-diffusion analyte distribution. In an embodiment, the generated model for each of the plurality of excitation lights is a mathematical function. Furthermore, the mathematical function may be a three-dimensional function, wherein the mathematical function may represent the spatial distribution of the analyte provided on a two-dimensional plane (for example, an x-y plane) and a third dimension thereof may be indicative of the temporal distribution of analyte. Subsequently, the third dimension of the mathematical function may be projected onto the two-dimensional plane to provide a two-dimensional mathematical function. Moreover, the two-dimensional mathematical function may be similar to a two-dimensional image. Therefore, the generated model for each of the plurality of excitation lights is a mathematical function representative of the analyte distribution in the well (specifically, of secretory footprints or fluorospots of the at least one analyte) for each of the at least one excitation light. Further, it is to be understood that a wavelength of fluorospots representing different analytes is different. Specifically, each generated model of analyte release distribution represents distribution of a distinct analyte in the well, and such distribution is detected by way of illuminating the well with a specific excitation light, and capturing the at least one image of the well, in raw image format, for the specific excitation light to generate the model of analyte release distribution for the distinct analyte. For example, two models (G1 and G2) of analyte release distribution in a well for two excitation lights (L3 and L4) may be generated. In such example, the model G1 may represent distribution of analyte A1 in the well and the model G2 may represent distribution of analyte A2 in the well. Therefore, a wavelength of fluorospots of analyte A1 in the model G1 is different from a wavelength of fluorospots of analyte A2 in the model G2.

Optionally, the method further comprises generating an X-Y table associated with the X-Y plane of the assay plate and obtaining the fluorescent intensity at the at least one spatially defined fluorospot based on the generated X-Y table. The term "X-Y table" relates to motorized linear slides with a linear motion, horizontal or vertical. Specifically, the X-Y table provides horizontal motion, i.e. along an X and Y axis of an XY plane, for an automated machinery. The XY plane of the assay plate includes a plurality of wells separated by a predefined distance. In an embodiment, the method of the present disclosure enables detection of data corresponding to the well coordinates, depth of well, centre of well and the exact position of the well borders. Optionally, such data may also include fluorospot size, peripheral distance between adjacent wells, distance from the center of at least two adjacent wells. In another embodiment, the X-Y table associated with the X-Y plane of the assay plate enables measuring the distance from the center of at least two adjacent wells. More optionally, the X-Y table is generated by employing a calibration algorithm. Specifically, the calibration algorithm is developed to calibrate the X-Y table. More specifically, the calibration algorithm is developed to calibrate and re-calibrate the X-Y table upon multiple series of rounds. In an embodiment, the calibration algorithm is programmed to visit every fluorospot on the XY plane of the assay plate. In yet another embodiment, the data corresponding to the well coordinates, depth of well, centre of well and the exact position of the well borders, fluorospot size, peripheral distance between adjacent wells, distance between the centers of two adjacent wells and so on, are predefined/preset to fully automate the process. Alternatively, additionally, the calibration algorithm is accessible for modification by a user by way of receiving manual inputs from the user of the system. Beneficially, fully (or semi) automated system provides benefits of time-efficiency and reduction in wrong calibration. In an embodiment, deconvolution of the captured at least one image of the well is an image processing technique that is implemented in order to sharpen the captured at least one image of the well for each of the at least one excitation light, by removing blurring caused by the diffusion and imaging equipment. Specifically, deconvolution may be implemented in order to determine an image among the captured at least one image for the given excitation light, wherein the determined image represents the pre-diffusion analyte distribution for the given excitation light. Such determined image is considered to be one which is most closely representative of the pre-diffusion analyte distribution among the captured at least one image for the given excitation light. More specifically, such deconvolution is performed on the captured at least one image for each of the at least one excitation light, thereby, taking into account both the spatially located analyte sources and temporal distribution represented by the at least one image. Further in an embodiment, an input of such deconvolution is the captured at least one image for the at least one excitation light, and an output of such deconvolution step is an image representing the pre-diffusion analyte distribution for each of the given excitation light. In another embodiment, an input of such deconvolution is the mathematical model of the analyte release distribution and the output of such deconvolution step is an image representing the pre-diffusion analyte distribution provided by multidimensional deconvolution.

According to an embodiment, deconvolving the captured at least one image of the well comprises implementing at least one of: sparsity-promoting regularization, multiplicative update rules, forward-backward proximal gradient algorithms. Specifically, at least one of the aforementioned algorithms may be employed in order to estimate the pre-diffusion analyte distribution for each of the at least one excitation light. For example, sparsity-promoting regularization may be implemented in form of l1-regularization or group-sparsity regularization based on (non-squared) form of l2-regularization over the captured at least one image for the given excitation light, for implementing regularization among the at least one image during such deconvolution. In another example, multiplicative update rules and/or forward-backward proximal gradient algorithms may facilitate optimization of variables during such deconvolution. Examples of forward-backward proximal gradient algorithms include, but are not limited to, iterative shrinkage-thresholding algorithms (ISTA), and the accelerated proximal gradient algorithms (FISTA).

Optionally, the method further comprises identifying a centre of the well for determining the spatially defined fluorospot. Specifically, local maxima at the center of each well is known as a calibration point or a hard spot or a spatially defined fluorospot. In an embodiment, detecting the at least one potential analyte release site based on local maxima in the pre-diffusion analyte distribution, may be implemented using conventional mathematical formulae and image processing functions for determining local maxima and evaluating the image representing the pre-diffusion analyte distribution, respectively.

In an embodiment, generation of the model of analyte release distribution in the well for a given excitation light comprises optimizing the pre-diffusion analyte distribution based on the detected at least one potential release site to generate the model of analyte release distribution in the well for the given excitation light. Optionally, optimizing the pre-diffusion analyte distribution relates to refitting the image representing the pre-diffusion analyte distribution based on the detected at least one potential analyte release site. Specifically, in such optimization, a constraint is added to the image representing the pre-diffusion analyte distribution, wherein the constraint is that analytes may be released only from the detected at least one potential analyte release site. According to an embodiment, optimizing the pre-diffusion analyte distribution based on the detected at least one potential analyte release site, is implemented iteratively at least once, and comprises employing at least one of: alternating direction methods, multiplicative update rules, forward-backward proximal gradient algorithms. Examples of the alternating direction methods include, but are not limited to, Douglas-Rachford alternating direction methods, iterative shrinkage-thresholding algorithms (ISTA), and split inexact Uzawa methods. Examples of the multiplicative update rules include, but are not limited to, Exponentiated gradient update rules, and multiplicative updates for positivity constrained quadratic programs.

In an example, optimizing a pre-diffusion analyte distribution for an excitation light L5 is implemented in two passes, wherein in a first pass, all pixels of an image representing the pre-diffusion analyte distribution for the excitation light L5 are considered as potential analyte release sites, and in a second pass, by employing at least one of the aforesaid algorithms/rules, a number of pixels considered as potential analyte release sites is reduced.

Therefore, it is to be understood that the generated model of analyte release distribution in the well for each of the plurality of excitation lights is generated in a form of a mathematical function.

In an embodiment, generating the model of analyte release distribution in the well for each of the plurality of excitation lights further comprises modifying the generated model of analyte release distribution in the well for each of the at least one excitation light, to analyse at least one fluorospot therein. Specifically, such modification may relate to gating or pruning of the at least one fluorospot in the generated model of analyte release distribution in the well for each of the at least one excitation light. Further, such modification may be performed to set 'cut-offs' to be employed to exclude and/or include the at least one fluorospot detected in the generated model of analyte release distribution in the well for each of the at least one excitation light. More specifically, such modification may facilitate a user to select the at least one fluorospot for analysis of attributes such as secretion intensity (or amount of analyte secretion) of the cells. For example, by modifying the generated model of analyte release distribution in the well for each of the at least one excitation light, the user can separately study and calculate an amount of the at least one analyte secreted by the cells under investigation.

According to an embodiment, modifying the model of analyte release distribution in the well, is based on at least one user-selectable parameter, wherein the at least one parameter is selected from a group comprising: fluorospot/fluorescent intensity, fluorospot size, estimated amount of analyte release, fluorospot colour, area of interest in the well. Specifically, upon selection of the at least one parameter, the user may specify a value of the selected at least one parameter as a measure of sensitivity of fluorospot detection/analysis. In an example, for a given excitation light L6, the user may select a parameter, such as area of interest in the well, and specify that only fluorospots in a left half of the well may be analysed. Optionally, in such example, the user may specify that the fluorospots along a periphery of the well may be discarded to prevent unwanted artefacts from being analysed. In another example, for the given excitation light L6, the user may select a parameter, such as fluorospot size, and specify that only fluorospots of radius greater than 30 micrometres may be analysed.

Therefore, it is to be understood that the modified model of analyte release distribution in the well for each of the plurality of excitation lights is provided in a form of a mathematical function.

Optionally, the method further comprises obtaining the fluorescent intensity at the at least one spatially defined fluorospot. More optionally, the fluorescent intensity at the at least one spatially defined fluorospot is obtained based on the generated X-Y table. Specifically, a spatially defined fluorospot is identified from the generated X-Y table that emits or radiates fluorescent of high intensity.

The method further comprises clustering a plurality of co-positioned fluorospots as a multiple secretion fluorospot, wherein the clustering is performed for all generated models of analyte release distribution, and wherein the clustering determines at least one multiple secretion fluorospot. Specifically, all generated models of analyte release distribution are processed to identify a plurality of fluorospots of different analytes that are positioned at a same location (for example, at same pixel coordinates) and/or proximal to each other. Further, in such instance, the plurality of fluorospots may be considered proximal to each other if their respective locations lie within a predetermined distance from each other. Specifically, such predetermined distance may be a maximal distance between fluorospots that can be clustered together. Optionally, such predetermined distance may be specified by the user. In an embodiment, clustering the plurality of co-positioned fluorospots employs a distance-based hierarchical clustering algorithm. Specifically, the distance-based hierarchical clustering algorithm is contiguity constrained, thereby, preventing proximal fluorospots of a same generated model of analyte release distribution from being clustered together.

It is to be understood that the term 'multiple secretion fluorospot' used herein relates to a secretory footprint of a plurality of analytes that are secreted from a single cell. Therefore, the plurality of co-positioned fluorospots for all generated models of analyte release distribution, represent the plurality of analytes that are secreted from the single cell. Further, the at least one multiple secretion fluorospot determined by aforesaid clustering relate to at least one cell that secretes the plurality of analytes.

According to an embodiment, the method may further comprise displaying a resultant model of analyte release distribution in the well, wherein the resultant model comprises the detected at least one fluorospot, and wherein single secretion fluorospots and multiple secretion fluorospots are represented distinctly. Specifically, the resultant model of analyte release distribution in the well relates to a resultant image that is an overlay of images of the generated models of analyte release distribution, for each of the at least one excitation light. More specifically, since the wavelength of fluorospots for different analytes is different, in the resultant model of analyte release distribution in the well, a wavelength of multiple secretion fluorospots may be a combination of wavelengths of fluorospots of its constituent analytes. For example, there may exist two modified models of analyte release distribution in a well to analyse two analytes (such as analytes A3 and A4). In such example, a wavelength of fluorospots of analyte A3 may correspond to a green colour, and a wavelength of fluorospots of analyte A4 may correspond to a red colour. Thereafter, in a resultant model of analyte release distribution in the well, there exist single secretion fluorospots (of each of the analytes A3 and A4) and multiple secretion fluorospots (of both analytes A3 and A4).

As mentioned previously, the present disclosure describes the system for analysing fluorospot assays. Specifically, the described system is employed for implementing the aforementioned method for analysing fluorospot assays.

The system comprises a light source arrangement configured to generate at least one excitation light, wherein at a given time, the light source arrangement generates only one excitation light. In an embodiment, the light source arrangement comprises at least one light source positioned on an actuator arrangement, wherein the at least one light source is implemented by way of at least one of: Light Emitting Diode, halogen light source, xenon light source, laser light source. For example, the light source arrangement may comprise 5 light sources positioned on a motorized actuator arrangement, wherein the motorized actuator arrangement may be rotatable, tiltable, or displaceable (horizontally and/or vertically).

Further, the system comprises a collimation arrangement positioned on an optical path of a generated excitation light, wherein the collimation arrangement is configured to collimate the generated excitation light. Specifically, the collimation arrangement makes rays of the plurality of excitation lights parallel to each other. In an example, the collimation arrangement may be at least one collimation lens.

Furthermore, the system comprises a multiband beam splitter positioned on an optical path of the collimated excitation light, the multiband beam splitter being supported by a support arrangement. The multiband beam splitter is configured to reflect the collimated excitation light onto an assay plate for illuminating a well of the assay plate having a plurality of wells, receive a reflection of the excitation light and an emitted light from the assay plate, and reflect a portion of the reflected excitation light whilst transmitting a remaining portion of the reflected excitation light and the emitted light to a filtering arrangement. Specifically, the multiband beam splitter receives the reflection of the excitation light mixed with the emitted light from the assay plate, but is unable to completely block the reflection of the excitation light from passing therethrough. Therefore, the portion of the reflected excitation light that is reflected from the multiband beam splitter relates to a part of the reflected excitation light that is blocked from passing through the multiband beam splitter. Further, the remaining portion of the reflected excitation light that is transmitted through the multiband beam splitter relates to remnants of the reflected excitation light that do not get blocked from through transmission. As described previously, the emitted light relates to fluorescence emitted from an analyte upon illumination by the collimated excitation light. Therefore, different emitted lights emitted from different analytes are passed through the multiband beam splitter.

In an embodiment, the assay plate is positioned at a right angle with respect to the multiband beam splitter. Therefore, the multiband beam splitter may reflect the collimated excitation light by an angle of approximately 90 degrees onto the assay plate for illuminating the well of the assay plate.

According to an embodiment, the multiband beam splitter is implemented by way of at least one of: a transparent mirror, a semitransparent mirror, a prism, a dichroic mirror. According to another embodiment, the support arrangement is a filter cube. Specifically, the filter cube may be a semitransparent or a transparent cubical structure configured to accommodate and support the multiband beam splitter therein. For example, in the system, a dichoric mirror may be mounted diagonally within a filter cube.

The system further comprises the filtering arrangement comprising a filter wheel and at least one emission filter, wherein the filter wheel is configured to accommodate the at least one emission filter therein. The at least one emission filter is configured to remove the remaining portion of the reflected excitation light received from the multiband beam splitter, and filter the emitted light whilst transmitting the emitted light to an optic arrangement. Specifically, the filter wheel is a rotatable device including at least one housing to accommodate the at least one emission filter therein. More specifically, the at least one emission filter may be configured to block light of any wavelength other than that of the emitted light.

Further, the system comprises the optical arrangement configured to direct the filtered emitted light onto an imaging device. Specifically, the optical arrangement may include at least one optical element to change the optical path of the filtered emitted light, so as to focus the filtered emitted light on to the imaging device. In an embodiment, the optical arrangement comprises at least one of: telecentric lens, macro lens. Optionally, the optical arrangement may also comprise optical elements such as mirrors, prisms, lenses, and the like.

The system comprises the imaging device configured to capture at least one image of the well, in raw image format, for each of the at least one excitation light. Specifically, the imaging device is selected from any one of: a high-dynamic-range imaging device, a low-dynamic-range imaging device, a digital camera. As mentioned previously, the present disclosure employs an HDR imaging device configured to capture the at least one image of the well, in raw image format, for each of the at least one excitation light. More specifically, the imaging device receives the filtered emitted light from the optical arrangement onto an image sensor of the imaging device, to capture the at least one image. In an embodiment, the imaging device may capture the at least one image in grayscale. Specifically, higher resolution grayscale images are captured by employing raw image format. Beneficially, images captured in raw image format are in unprocessed form as compared to images of other formats such as Joint Photographic Experts Group (JPEG) format, and are therefore free from colourspace-dependent encoding. In another embodiment, the imaging device may capture the at least one image as coloured images.

Furthermore, the system comprises a processing module coupled to the imaging device, wherein the processing module is configured to generate the model of analyte release distribution in the well for each of the at least one excitation light, and cluster the plurality of co-positioned fluorospots as a multiple secretion fluorospot, wherein the clustering is performed for all generated models of analyte release distribution, and wherein the clustering determines at least one multiple secretion fluorospot.

Optionally, in this regard, the processing module is further configured to deconvolve the captured at least one image of the well for the given excitation light to estimate a pre-analyte distribution, and detect at least one potential analyte release site based on local maxima in the pre-diffusion analyte distribution.

Optionally, the system further comprises a tuner, wherein the tuner is operable to move horizontally along the X-Y plane of the assay plate to the at least one spatially defined fluorospot, and wherein the sensor is operable to obtain the fluorescent intensity associated with the at least one spatially defined fluorospot. Specifically, the tuner visits every spatially defined fluorospot on the XY plane of the assay plate. More specifically, the sensor coupled to the tuner records the fluorescent intensity associated with the at least one spatially defined fluorospot. Furthermore, the spatially defined fluorospot with a high fluorescent intensity is counted and its position, as obtained by the generated XY table, is provided to one or more components of the system for further use, such as data processing.

Optionally, the system further comprises a controller operatively coupled to the tuner. More optionally, the controller is operable to preset the data corresponding to the well coordinates, depth of well, centre of well and the exact position of the well borders, fluorospot size, peripheral distance between adjacent wells, distance between the centers of two adjacent wells and so on, are predefined/preset to fully automate the process.

Furthermore, the controller is configured to generate an X-Y table associated with movement of the tuner horizontally along the X-Y plane of the assay plate. Specifically, the controller is operable to generate the X-Y table based on the preset data corresponding to the well coordinates, depth of well, centre of well and the exact position of the well borders, fluorospot size, peripheral distance between adjacent wells, distance between the centers of two adjacent wells and so on. The controller is further operable to provide the generated X-Y table to the tuner, and wherein the tuner is configured to move horizontally along the X-Y plane of the assay plate based on the provided X-Y table. Specifically, the generated X-Y table guides the tuner to visit the multiple fluorospots in a predefined linear motion, preferably horizontal, over the XY plane of the assay plate. More specifically, the horizontal movement of the tuner along the X-Y plane of the assay plate based on the provided X-Y table enables assessing all the wells of the assay plate and determining the spatially defined fluorospots with high fluorescent intensity.

Optionally, the controller is operable to generate the X-Y table by employing a calibration algorithm. As mentioned previously, the calibration algorithm comprises data corresponding to the well coordinates, depth of well, centre of well and the exact position of the well borders, fluorospot size, peripheral distance between adjacent wells, distance between the centers of two adjacent wells and so on preset/predefined to fully automate the process. Specifically, the calibration algorithm governs the movement of tuner over every fluorospot on the XY plane of the assay plate.

Optionally, the controller is further operable to identify a centre of the well. Specifically, the calibration algorithm is developed to identify the area of interest in the assay plate for detection of fluorospots. More specifically, the fluorospots are counted within the area of interest, and the fluorospots falling outside the area of interest are not counted while determining the concentration of at least one fluorophore-detected analyte in the spatially defined area of the well. Furthermore, the calibration algorithm has an auto-centering functionality that determines the centers of the well for measurements of fluorescent intensity. In this case, the calibration algorithm calculates the distance between the center of two wells to identify the calibration points. The calibration algorithm moves the tuner to the calibration points, where the sensor of the tuner measures the fluorescent intensity. In an embodiment, the calibration algorithm calibrates and recalibrates the X-Y table to avoid the saturation of the sensor over a period of time of use.

Optionally, the controller is further operable to detect a deviation in the generated X-Y table and the movement of the tuner. Specifically, the calibration algorithm detects the difference in predefined distance from the centers of at least two adjacent wells and the position of the tuner. More specifically, the deviation in the generated X-Y table and the movement of the tuner is an indication to a wrong calibration. For example. If the distance between the center of two adjacent wells (W0 and W1) on an assay plate (W) is 1.25 cm, and the same is preset in the X-Y table; however, the tuner moves to a well W1 that is 1 cm away from the center of the well W0, in such a case, the controller is operable to detects a deviation of 0.25 cm in the generated X-Y table and the movement of the tuner.

Furthermore, the controller is also operable to provide, based on the detected deviation, a correction for the movement of the tuner. Specifically, the controller corrects any deviation in the generated X-Y table and the movement of the tuner. More specifically, the controller employs an auto-centering module for the correction of the movement of the tuner. More specifically, the auto-centering module corrects the movement of the tuner and places the tuner right above the spatially defined fluorospot. For instance, in the above example, for a deviation of 0.25 cm in the generated X-Y table and the movement of the tuner is corrected by the autocentering module by shifting the tuner right above the spatially defined fluorospot.

In an embodiment, the calibration algorithm includes a circular Area of Interest (AOI) that constrains the area in which spatially defined fluorospots are detected and counted in each image captured. Fluorospots detected outside of the AOI are not counted. Specifically, a feature in the calibration algorithm identifies the well border and automatically places the AOI in the center position of the well. More specifically, as the well centers deviates from well-to-well and from plate-to-plate, the well centering algorithm is absolutely essential in order to generate a consistent data.

Furthermore, optionally, the processing module is configured to optimize the pre-diffusion analyte distribution based on the detected at least one potential release site and modify the generated model of analyte release distribution in the well for each of the at least one excitation analyte, to analyse at least one fluorospot therein.

In an embodiment, the system further comprises at least one excitation filter positioned on an optical path of the collimated excitation light, wherein the at least one excitation filter is configured to filter the collimated excitation light. Specifically, the at least one excitation filter may be configured to the wavelengths of the plurality of excitation lights such that, at a given time, an excitation filter may only pass an excitation light of a desired wavelength whilst blocking light of other wavelengths from passing therethrough. Therefore, the at least one excitation filter purifies the collimated excitation light by blocking undesired light components. In such instance, a distinct excitation filter may be employed for a distinct excitation light. Optionally, the excitation filter may comprise a filter wheel.

In an embodiment, the system may further comprise a visualization module coupled to the imaging device and the processing module, wherein the visualization module comprises a user interface rendered on a computing device associated with a user, and wherein the visualization module is configured to perform at least of: display the captured at least one image for each of the at least one excitation light, display the generated model of analyte release distribution in the well for each of the at least one excitation light, receive user input to control operation of the processing module, display a resultant model of analyte release distribution in the well. Specifically, the visualization module may be operable by the user of the system for viewing the analysis of assays. In an example, the user may modify the generated model of analyte release distribution in the well for each of the plurality of excitation lights by interacting with the user interface (for example, via touch input, keypad input, mouse input, and the like) to select a parameter such as area of interest in the well, and specify the value of the parameter (such as, a left half of the well). Examples of the computing device associated with the user include, but are not limited to, a smartphone, a tablet computer, a desktop computer, a notebook computer, and a personal digital assistant.

In an embodiment, the system may further comprise a mask for removing noise from the at least one excitation light. The term 'noise' relates to random disturbance that influence the overall fluorospot count. Noise may result from artefacts, such as hair, dust, fibers and the like, that enter into the wells of the assay plate. Such noise can get counted by the algorithm or software of the imaging device and result in false positive and/or false negatives in the overall fluorospot count. It is therefore necessary to remove the false positives and false negatives one by one, ensuring a noise-free fluorospot count. Noise removal is performed by adding a layer of paint, such as a mask, to the wells influenced with noise, and is configured to exclude noise behind the mask from the overall fluorospot count. Specifically, the term 'mask' relates to a practical approach for removing noise from an image. Beneficially, the mask excludes such artefacts from the spot-count, wherein all spots behind the mask are excluded from the overall spot-count. Subsequently, the noise is subtracted from the fluorescent intensity to obtain the net fluorescent intensity. The obtained net fluorescent intensity of each well of the assay plate is saved in any one of image file formats, including, but not limited to, Joint Photographic Experts Group format, Tagged Image File Format, Portable Network Graphics format, and Graphics Interchange Format.

For example, when an image of the plate is saved for example in a format such as Joint Photographic Experts Group (JPEG) format, a special Joint Photographic Experts Group (JPEG) image is created, namely Mask (or Mask.jpeg) depicting the locations on the well plate where the mask was added. Beneficially, a 'history file' is created that records each action performed over the image. Additionally, history file is used to access the possible alterations done on the saved image file.

Furthermore, the mask for removing noise from the plurality of excitation lights is operable to be removed from the system arrangement if required. Specifically, the added layer of paint is operable to be removed, as desired by the user, by simply accessing saved image of the plate and removing the mask to obtain the original data, comprising the fluorospots along with the potential noise associated with the fluorospots. It will be appreciated that in the mask implementation or removal process, no action or data is ever erased and each action is recorded in a history file. The history file records each change made in the process of analysing the FluoroSPot assays.

In yet another aspect, an embodiment of the present disclosure provides a method for analysing spatially defined FluoroSpot assays, the method comprising determining the concentration of at least one fluorophore-detected analyte in a spatially defined area of the well; wherein determination of the concentration of the analyte includes:
(a) identifying the at least one spatially defined fluorospot;
(b) sensing the at least one spatially defined fluorospot to obtain fluorescent intensity associated with the at least one spatially defined fluorospot; and
(c) correlating the obtained fluorescent intensity associated with the at least one spatially defined fluorospot with the concentration of at least one fluorophore-detected analyte in the spatially defined area of the well.

In yet another aspect, an embodiment of the present disclosure provides a system for analysing spatially defined fluorospot assays, the system comprising a sensor arrangement to determine the concentration of at least one fluorophore-detected analyte in a spatially defined area of the well, wherein the sensor arrangement comprises:

(a) a sensor operable to read at least one spatially defined fluorospot; and (b) a tuner configured to obtain fluorescent intensity associated with the at least one spatially defined fluorospot, characterized in that the tuner is further configured to correlate the obtained fluorescent intensity associated with the at least one spatially defined fluorospot with the concentration of at least one fluorophore-detected analyte in the spatially defined area of the well.

Specifically, fluorospot assays can be analyzed for detecting analytes secreted by the cells as well as for determining the concentration of at least one fluorophore-detected analyte in the spatially defined area of the well. Optionally, the analyte includes at least one of: a serum sample, a plasma sample, a urine sample, a liquor sample, a viral particle, a protein, a cell supernatant, at least one potential analyte in the well. Specifically, the analytes include, but are not limited to, cytokines, and immunoglobulins. More specifically, the various samples, such as the serum sample, the plasma sample, the urine sample, the liquor sample, the viral particle, the protein, the cell supernatant, the at least one potential analyte release site in the well, can be cultured within the assay plate to increase the concentration of the analyte secreted by the sample of cells.

The term 'concentration' relates to a measurable property. Specifically, the concentration can be measured as mass concentration, volume concentration, molar concentration, number concentration, and so forth. Furthermore, the concentration of a solute or solvent in a solution can range from diluted to concentrated, depending on the amount of the solute or solvent in the solution. Specifically, the concentration of analyte is determined from the model of analyte release distribution in the well generated for a given excitation light.

The method for determining the concentration of at least one fluorophore-detected analyte in the spatially defined area of the well comprises identifying the at least one spatially defined fluorospot. In an embodiment, the concentration of the at least one fluorophore-detected analyte in the spatially defined area of the well is based on at least one user-selectable parameter, wherein the at least one parameter is selected from a group comprising: fluorospot/fluorescent intensity, fluorospot size, estimated amount of analyte release, fluorospot colour, area of interest in the well. Specifically, upon selection of the at least one parameter, the user may specify a value of the selected at least one parameter as a measure of sensitivity of fluorospot detection/analysis. More specifically, the concentration of the at least one fluorophore-detected analyte in the spatially defined area of the well is based on fluorospot/fluorescent intensity. In an example, for the excitation light L7, the user may select one or more parameters, such as fluorospot/fluorescent intensity, fluorospot colour and area of interest, and specify that only fluorospots with high intensity of green colour are to be selected within the left half of the well.

Further, the method comprises sensing the at least one spatially defined fluorospot to obtain fluorescent intensity associated with the at least one spatially defined fluorospot. The spatially defined fluorospot provides a measurable fluorescent signal that is detected by a sensor. Optionally, the concentration of the at least one fluorophore-detected analyte distributed in the spatially defined area of the well is based on fluorescent intensity. It will be appreciated that the concentration of the fluorophore-detected analyte is proportional to the fluorescence intensity, and preferably darkness of colour of fluorescence.

Optionally, the method further comprises obtaining the fluorescent intensity at the at least one spatially defined fluorospot. Moreover, obtaining the fluorescent intensity at the at least one spatially defined fluorospot includes setting 'cut-offs'. Specifically, the cut-off is employed to exclude and/or include the at least one spatially defined fluorospot detected in the generated model of analyte release distribution for each of the at least one excitation light. More optionally, such modification may facilitate sensing the at least one spatially defined fluorospot for analysis of attributes such as secretion intensity and/or concentration of analyte secreted by the cells. Furthermore, such modification may be based on at least one user-selectable parameter, wherein the at least one parameter is selected from a group comprising: fluorospot/fluorescent intensity, fluorospot size, estimated amount of analyte release, fluorospot colour, area of interest in the well. Optionally, by combining the fluorescent intensity and capturing images of the well, it is possible to provide high sensitivity and an excellent measuring range for the concentration of the fluorophore-detected analyte. Sensing the at least one spatially defined fluorospot to obtain fluorescent intensity associated with the at least one spatially defined fluorospot includes sensing the fluorescent intensity at the area of interest in the well, preferably at the centre. Furthermore, the method further comprises identifying a center of the well for determining the spatially defined fluorospot. The "center of well" is determined based on the coordinates of the well obtained by analysing the captured image of the well. Specifically, sensing the at least one fluorospot to obtain fluorescent intensity associated with the at least one spatially defined fluorospot is performed automatically, without requiring direct and frequent manual interventions. More specifically, sensing the at least one fluorospot to obtain fluorescent intensity associated with the at least one fluorospot excludes the fluorescent intensity associated with the at least one fluorospot that is a result of simple wall reflections. Optionally, sensing the at least one fluorospot to obtain fluorescent intensity associated with the at least one fluorospot is performed around the area of interest, preferably a circular area of interest. In an example, fluorospots exhibiting high intensity of green colour are sensed for analyte A5 in a predefined circular area of interest. It is understood that flurospots outside the area of interest are not included in the sensing of at least one fluorospot to obtain fluorescent intensity.

Optionally, the method further comprises generating an X-Y table associated with the X-Y plane of the assay plate. In an embodiment, the method of the present disclosure enables detection of data corresponding to the well coordinates, depth of well, centre of well and the exact position of the well borders, fluorospot size, peripheral distance between adjacent wells, distance from the center of at least two adjacent wells. Specifically, the method employs an automated machinery, such as a precision motor, that is configured to determine the distance from the center of at least two adjacent wells.

Optionally, the method further comprises obtaining the fluorescent intensity at the at least one spatially defined fluorospot. More optionally, the fluorescent intensity at the at least one spatially defined fluorospot is obtained based on the generated X-Y table. Specifically, a spatially defined fluorospot is identified from the generated X-Y table that emits or radiates fluorescent of high intensity. More specifically, the fluorescence intensity is measured by a fluorescence measuring instrument at the at least one spatially defined fluorospot.

Furthermore, the X-Y table is generated by employing a calibration algorithm. Specifically, the calibration algorithm is developed to calibrate the X-Y table. More specifically, the calibration algorithm is developed to calibrate and re-calibrate the X-Y table upon multiple series of rounds. In an embodiment, the calibration algorithm is programmed to move the sensor coupled to the tuner to every fluorospot. In another embodiment, the calibration algorithm is programmed to protect the sensor from over-current. Optionally, the data corresponding to the well coordinates, depth of well, centre of well and the exact position of the well borders, fluorospot size, peripheral distance between adjacent wells, distance between the centers of two adjacent wells and so on, are predefined/preset in the sensor to fully automate the process. Alternatively, additionally, the sensor is configured to receive manual inputs from a user of the fluorescence measuring instrument.

The method further comprises correlating the obtained fluorescent intensity associated with the at least one spatially defined fluorospot with the concentration of at least one fluorophore-detected analyte distributed in the spatially defined area of the well. Specifically, the concentration of the at least one fluorophore-detected analyte in the spatially defined area of the well is proportional to the fluorescent signal detected by the sensor. The obtained fluorescent intensity may be correlated with the concentration of at least one fluorophore-detected analyte in the spatially defined area of the well. In an embodiment, the concentration of at least one fluorophore-detected analyte in the spatially defined area of the well is a mathematical function. Furthermore, the mathematical function may represent analyte concentration in the well. In an example, a net fluorescent intensity of fluorospots with a wavelength corresponding to a green colour can be correlated to an analyte A6 and its concentration in the well. In another example, the concentration of A6 in the well is determined as one or more of: mass concentration, volume concentration, molar concentration, number concentration, and so forth. In yet another example, the concentration of A6 in the well is 3 microgram of analyte A6 per litre of solvent. It is to be understood that although the method described herein relates to analysis of one well of the assay plate, the method may be implemented to analyse more than one well of the assay plate. In such instance, two models (G3 and G4) of analyte release distribution in a well for two excitation lights (L8 and L9) may be generated. In such example, the model G3 may represent distribution of analyte A7 in the well and the model G4 may represent distribution of analyte A8 in the well. Therefore, a wavelength of fluorospots of analyte A7 in the model G3 is different from a wavelength of fluorospots of analyte A8 in the model G4. Furthermore, the concentration C1 of the analyte A7 in the model G3 is different from the concentration C2 of the analyte A8 in the model G4.

Optionally, the method further comprises removing noise from the at least one excitation light. As mentioned previously, noise removal is performed by employing the mask. Beneficially, the mask excludes such artefacts from the spot-count, wherein all spots behind the mask are excluded from the overall spot-count. Subsequently, the noise is subtracted from the fluorescent intensity to obtain the net fluorescent intensity. The obtained net fluorescent intensity of each well of the assay plate is saved in any one of image file formats, including, but not limited to, Joint Photographic Experts Group format, Tagged Image File Format, Portable Network Graphics format, and Graphics Interchange Format.

As mentioned previously, the present disclosure describes the system for analysing fluorospot assays, the system for determining the concentration of at least one fluorophore-detected analyte in the spatially defined area of the well. Specifically, the determination of at least one fluorophore-detected analyte requires employing a sensing arrangement to measure the fluorescent intensity of each well, and correlating the measured fluorescent intensity of each well with the concentration of the at least one fluorophore-detected analyte in the spatially defined area of the well. Specifically, the described system is employed for implementing the aforementioned method for analysing fluorospot assays.

The system for determining the concentration of at least one fluorophore-detected analyte in the spatially defined area of the well comprises the sensor operable to read the at least one spatially defined fluorospot. The term 'sensor' relates to a high precision measuring instrument configured to detect fluorescent intensity of varying wavelengths. Optionally, the sensor is operable to move to at least one fluorospot and determine the centre of the well to detect fluorescent intensity at each well. In an embodiment, the sensor converts the fluorescent intensity associated with the at least one spatially defined fluorospot into an electrical signal for quantifying the fluorescent intensity.

The sensor arrangement further comprises the tuner configured to obtain fluorescent intensity associated with the at least one spatially defined fluorospot. Specifically, the tuner is operatively coupled to the sensor and comprises high precision motors and the calibration algorithm. More specifically, the tuner is configured to access the data corresponding to the well coordinates, depth of well, centre of well and the exact position of the well borders. Subsequent to accessing the suitable fluorospot, the tuner places the sensor at a spatially defined fluorospot, where the sensor detects the at least one spatially defined fluorospot to obtain fluorescent intensity associated with the at least one spatially defined fluorospot.

Optionally, the tuner is configured to regulate current in the sensor arrangement, preferably in the sensor. Specifically, the tuner prevents the sensor from over-current induced by the fluorescent intensity while converting the fluorescent intensity into the electrical signal.

The tuner is further configured to correlate the obtained fluorescent intensity associated with the at least one spatially defined fluorospot with the concentration of at least one fluorophore-detected analyte in the spatially defined area of the well. The net fluorescent intensity is obtained by removing the noise from the obtained fluorescent intensity associated with the at least one spatially defined fluorospot. Optionally, the tuner is operable to remove noise from the at least one excitation light. As mentioned previously, noise removal is performed by employing the mask. Beneficially, the mask excludes such artefacts from the spot-count, wherein all spots behind the mask are excluded from the overall spot-count. Subsequently, the noise is subtracted from the obtained fluorescent intensity associated with the at least one spatially defined fluorospot to obtain the net fluorescent intensity. The net fluorescent intensity of each well of the assay plate is saved in any one of image file formats, including, but not limited to, Joint Photographic Experts Group format, Tagged Image File Format, Portable Network Graphics format, and Graphics Interchange Format. Furthermore, while saving an image of the net fluorescent intensity, a special Joint Photographic Experts Group (JPEG) image is created, namely Mask (or Mask.jpeg) depicting the locations on the well plate where the mask was added. Additionally, a 'history file' is created that records each action performed over the image. The history file is used to access the possible alterations done on the saved image file.

Furthermore, the mask for removing noise from the plurality of excitation lights is operable to be removed from the system arrangement if required. Specifically, the added layer of paint is operable to be removed, as desired by the user, by simply accessing saved image of the plate and removing the mask to obtain the original data, comprising the fluorospots along with the potential noise associated with the fluorospots. It will be appreciated that in the mask implementation or removal process, no action or data is ever erased and each action is recorded in a history file. The history file records each change made in the process of analysing the fluorospot assays.

Optionally, the system further comprises a controller operatively coupled to the tuner. The controller arrangement is operatively coupled to the tuner to help in determining the concentration of at least one fluorophore-detected analyte in the spatially defined area of the well. Furthermore, the controller is configured to generate an X-Y table associated with movement of the tuner horizontally along the X-Y plane of the assay plate. As mentioned previously, the X-Y table enables the tuner to move in a linear, preferably horizontal, direction and assess all the wells of the assay plate and determine the fluorospots with high fluorescent intensity. Optionally, the controller is operable to generate the X-Y table by employing the calibration algorithm. The calibration algorithm enables the controller to generate the X-Y table by presetting the data corresponding to the well coordinates, depth of well, centre of well and the exact position of the well borders, fluorospot size, peripheral distance between adjacent wells, distance from the centers of at least two adjacent wells and so on, in the controller.

The controller is further operable to provide the generated X-Y table to the tuner. The tuner is operable to move horizontally along the X-Y plane of the assay plate to the at least one spatially defined fluorospot, and wherein the sensor is operable to obtain the fluorescent intensity associated with the at least one spatially defined fluorospot. As mentioned previously, the X-Y table is generated by employing a calibration algorithm. The tuner is configured to move horizontally along the X-Y plane of the assay plate based on the provided X-Y table based on the calibration algorithm. The horizontal movement of the tuner along the X-Y plane of the assay plate based on the provided X-Y table enables assessing all the wells of the assay plate and determining the spatially defined fluorospots with high fluorescent intensity.

Optionally, the controller is further operable to identify a centre of the well. Specifically, the calibration algorithm is developed to identify the area of interest in the assay plate for detection of fluorospots. More specifically, the fluorospots are counted within the area of interest, and the fluorospots falling outside the area of interest are not counted while determining the concentration of at least one fluorophore-detected analyte in the spatially defined area of the well. Furthermore, the calibration algorithm has an auto-centering functionality that determines the centers of the well for measurements of fluorescent intensity. In this case, the calibration algorithm calculates the distance between the center of two wells to identify the calibration points. The calibration algorithm moves the tuner to the calibration points, where the sensor of the tuner measures the fluorescent intensity. In an embodiment, the calibration algorithm calibrates and recalibrates the X-Y table to avoid the saturation of the sensor over a period of time of use.

Optionally, the controller is further operable to detect a deviation in the generated X-Y table and the movement of the tuner. Specifically, the calibration algorithm detects the difference in predefined distance from the centers of at least two adjacent wells and the position of the tuner. More specifically, the deviation in the generated X-Y table and the movement of the tuner is an indication to a wrong calibration.

However, the controller is further operable to provide, based on the detected deviation, a correction for the movement of the tuner. Specifically, the controller possesses an auto-centering module for the correction of the movement of the tuner. More specifically, the auto-centering module corrects the movement of the tuner and places the tuner right above the spatially defined fluorospot. In an embodiment, the calibration algorithm includes a circular Area of Interest (AOI) that constrains the area in which spatially defined fluorospots are detected and counted in each image captured. Fluorospots detected outside of the AOI are not counted. Specifically, a feature in the calibration algorithm identifies the well border and automatically places the AOI in the center position of the well. More specifically, as the well centers deviates from well-to-well and from plate-to-plate, the well centering algorithm is absolutely essential in order to generate a consistent data. In an embodiment, the tuner may comprise an in-built sensor that is configured to detect the fluorospot/fluorescent intensity and convert it to the electrical signal corresponding to the fluorospot/fluorescent intensity.

In a yet another aspect, embodiments of the present disclosure provide a software product recorded on machine-readable non-transitory (non-transient) data storage media, wherein the software product is executable upon computing hardware for implementing the aforementioned method; in other words, the present disclosure provides a computer program product comprising a non-transitory computer-readable storage medium having computer-readable instructions stored thereon, the computer-readable instructions being executable by a computerized device comprising processing hardware to execute a method for analysing fluorospot assays.

DETAILED DESCRIPTION OF THE DRAWINGS

Referring to FIG. 1, illustrated is a schematic illustration of a system 100 for analysing assays, in accordance with an embodiment of the present disclosure. The system 100 includes a light source arrangement 102 configured to generate at least one excitation light, wherein at a given time, the light source arrangement 102 generates only one excitation light. As shown, the light source arrangement 102 includes at least one light source, depicted as light sources 104, 106, and 108 positioned on an actuator arrangement 110. For example, light sources 104-108 are implemented by way of Light Emitting Diodes. It is to be understood, that an excitation light generated from the light source 106 is depicted as dashed lines, and an optical path of the excitation light is depicted by use of arrows along the dashed lines. The system 100 includes a collimation arrangement 112 positioned on an optical path of the generated excitation light to collimate the generated excitation light, and may contain at least one excitation filter, depicted as excitation filter 114, to filter the collimated excitation light.

As shown, the system 100 includes a multiband beam splitter 116 positioned on an optical path of the filtered excitation light, the multiband beam splitter 116 being supported by a support arrangement 118. For example, the multiband beam splitter 116 is implemented by way of a dichroic mirror and the support arrangement 118 is a filter cube. As shown, the multiband beam splitter 116 reflects the filtered excitation light onto an assay plate 120 for illuminating a well of the assay plate 120 having a plurality of wells. The multiband beam splitter 116 is also configured to receive a reflection of the excitation light and an emitted light from the assay plate and reflect a portion of the reflected excitation light whilst transmitting a remaining portion of the reflected excitation light and the emitted light to a filtering arrangement 122. It is to be understood that a combination of the reflection of the excitation light and the emitted light, is depicted as a dashed-dot line having arrows (commonly known as a centre line).

The filtering arrangement 122 includes a filter wheel 124 and at least one emission filter (depicted as emission filters 126 and 128), wherein the filter wheel 124 is configured to accommodate the at least one emission filter 126-128 therein. As shown, the emission filter 126 is configured to remove the remaining portion of the reflected excitation light received from the multiband beam splitter 116 and filter the emitted light whilst transmitting the emitted light to an optic arrangement 130. It is to be understood that the filtered emitted light is depicted as a dotted line and an optical path of the filtered emitted light is depicted by use of arrows along the dotted lines. The optical arrangement 130 is configured to direct the filtered emitted light onto an imaging device 132. The system 100 further includes a processing module (not shown) coupled to the imaging device 132.

Figure 2A:
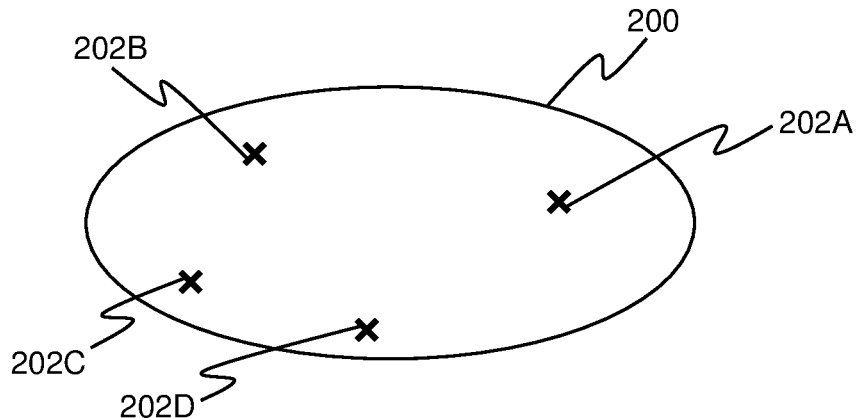
FIGS. 2A, 2B and 2C are schematic illustrations of images of a generated model of a first analyte release distribution, a generated model of a second analyte release distribution, and a resultant model of analyte release distribution in a well, respectively, in accordance with an embodiment of the present disclosure.
Figure 2B:
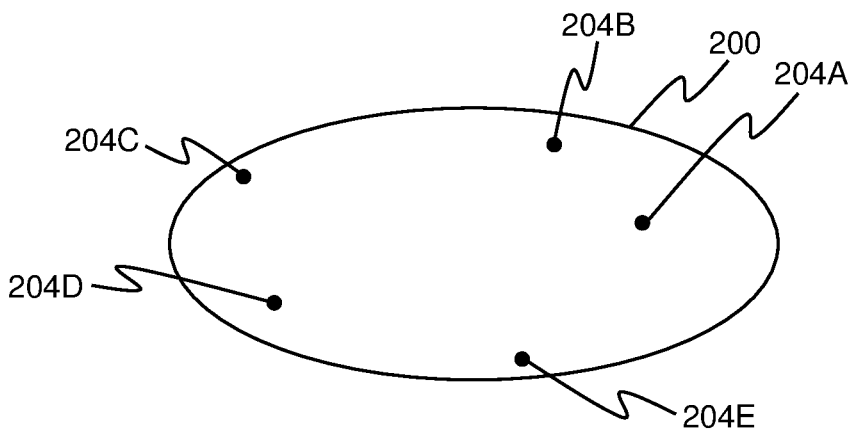
Figure 2C:
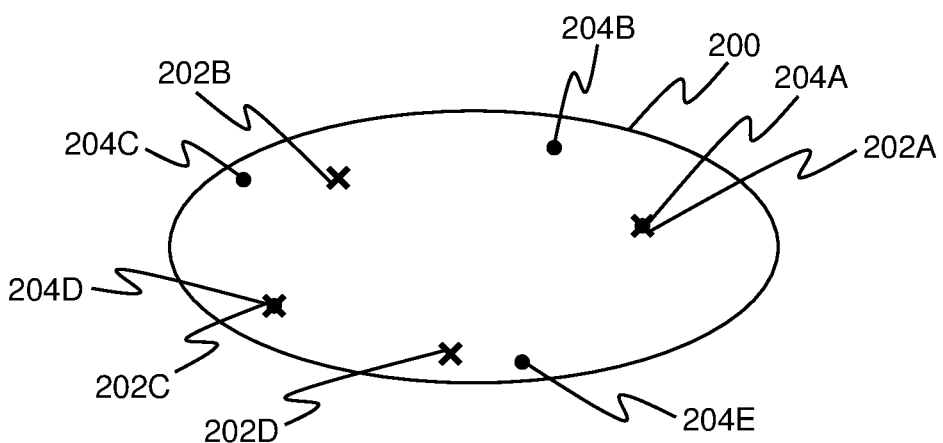

Referring to FIGS. 2A, 2B and 2C, illustrated are schematic illustrations of images of a generated model of a first analyte release distribution, a generated model of a second analyte release distribution, and a resultant model of analyte release distribution in a well 200, respectively, in accordance with an embodiment of the present disclosure.

With reference to FIG. 2A, illustrated is an image of the generated model of the first analyte release distribution in the well 200, in accordance with an embodiment of the present disclosure. As shown, a plurality of fluorospots 202A, 202B, 202C, and 202D of the first analyte are depicted as crosses.

With reference to FIG. 2B, illustrated is an image of the generated model of the second analyte release distribution in the well 200, in accordance with an embodiment of the present disclosure. As shown, a plurality of fluorospots 204A, 204B, 204C, 204D, and 204E of the second analyte are depicted as dots.

With reference to FIG. 2C, illustrated is an image of the resultant model of analyte release distribution in the well 200, in accordance with an embodiment of the present disclosure. As shown, FIG. 2C is an overly of images of FIGS. 2A and 2B, wherein the plurality of fluorospots 202A-D of the first analyte and the plurality of fluorospots 204A-E of the second analyte are depicted distinctly. As shown, the fluorospots 202A and 204A are co-positioned and are therefore determined as a first multiple secretion fluorospot. Similarly, the fluorospots 202C and 204D are co-positioned and are therefore determined as a second multiple secretion fluorospot.

FIGS. 2A, 2B and 2C are merely examples, which should not unduly limit the scope of the claims herein. A person skilled in the art will recognize many variations, alternatives, and modifications of embodiments of the present disclosure.

Figure 3:
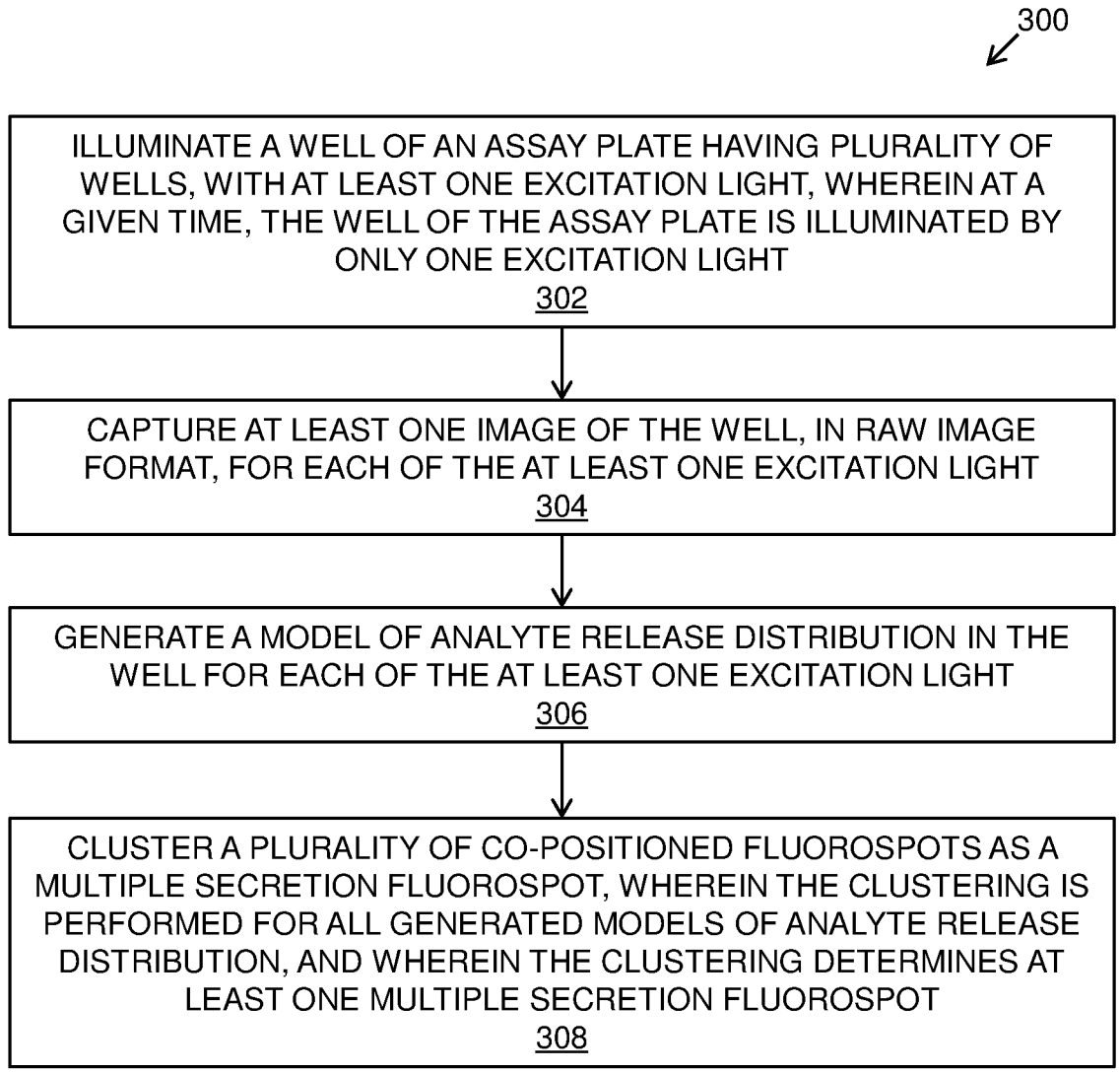
FIG. 3 illustrates steps of a method for analysing fluorospot assays, in accordance with an embodiment of the present disclosure.

Referring to FIG. 3, illustrated are steps of a method 300 for analysing assays, in accordance with an embodiment of the present disclosure. At step 302, a well of an assay plate having plurality of wells, is illuminated with at least one excitation light, wherein at a given time, the well of the assay plate is illuminated by only one excitation light. At step 304, at least one image of the well, in raw image format, is captured for each of the at least one excitation light. At step 306, a model of analyte release distribution in the well is generated for each of the at least one excitation light. The generation of the model of analyte release distribution in the well for a given excitation light comprises deconvolving the captured at least one image of the well for the given excitation light to estimate a pre-diffusion analyte distribution, wherein such deconvolution is performed prior to local diffusion of at least one analyte, and detecting at least one potential analyte release site based on local maxima in the pre-diffusion analyte distribution. At step 308, a plurality of co-positioned fluorospots are clustered as a multiple secretion fluorospot, wherein the clustering is performed for all generated models of analyte release distribution, and wherein the clustering determines at least one multiple secretion fluorospot.

The steps 302 to 308 are only illustrative and other alternatives can also be provided where one or more steps are added, one or more steps are removed, or one or more steps are provided in a different sequence without departing from the scope of the claims herein.

Figure 4:
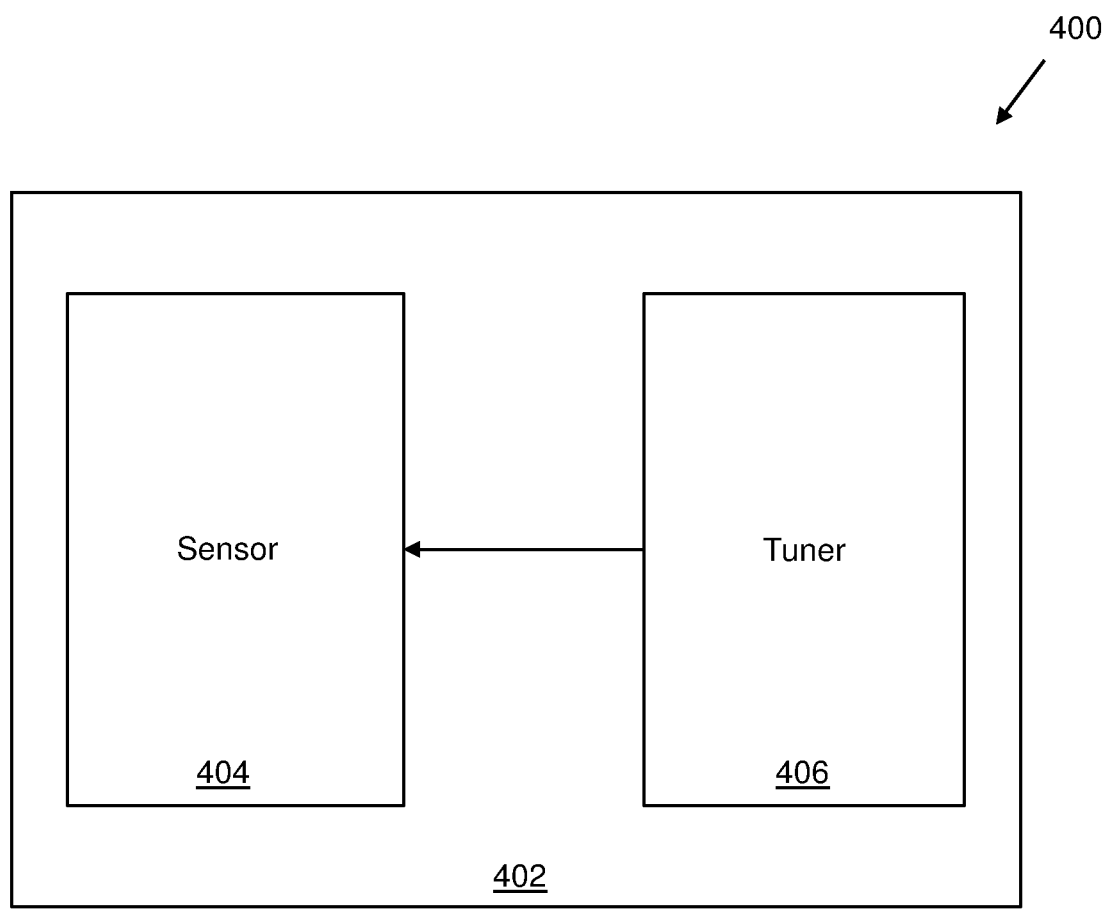
FIG. 4 is a schematic illustration of a system for determining the concentration of at least one fluorophore-detected analyte in a spatially defined area of the well, in accordance with an embodiment of the present disclosure.

Referring to FIG. 4, illustrated is a schematic illustration of a system 400 for analysing spatially defined fluorospot assays, in accordance with an embodiment of the present disclosure. The system 400 comprises a sensor arrangement 402 to determining the concentration of at least one fluorophore-detected analyte in the spatially defined area of the well. Furthermore, the sensor arrangement 402 comprises a sensor 404 operable to read at least one fluorospot. The sensor arrangement 402 further comprises a tuner arrangement 406 configured to obtain fluorescent intensity associated with the at least one spatially defined fluorospot. The tuner arrangement 406 is further configured to correlate the obtained fluorescent intensity associated with the at least one spatially defined fluorospot with the concentration of at least one fluorophore-detected analyte in the spatially defined area of the well.

Figure 5:
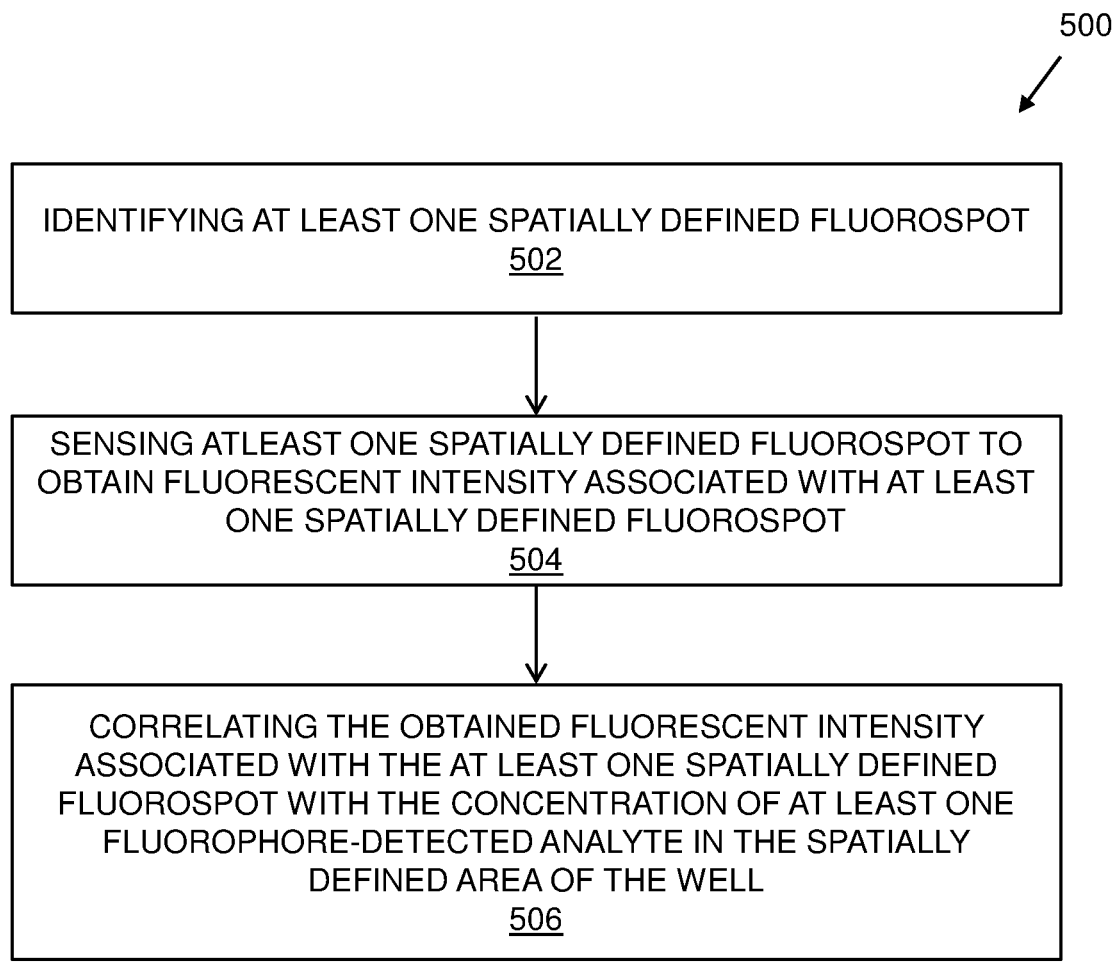
FIG. 5 illustrates steps of a method for determining the concentration of at least one fluorophore-detected analyte in a spatially defined area of the well, in accordance with an embodiment of the present disclosure.

Referring to FIG. 5, illustrated are steps of a method 500 for analysing spatially defined fluorospot assays, in accordance with an embodiment of the present disclosure. The method 500 comprises determining the concentration of at least one fluorophore-detected analyte in the spatially defined area of the well. At step 502, the at least one spatially defined fluorospot is identified. At step 504, the at least one spatially defined fluorospot is sensed to obtain fluorescent intensity associated with the at least one spatially defined fluorospot. At step 506, the obtained fluorescent intensity associated with the at least one spatially defined fluorospot is correlated with the concentration of at least one fluorophore-detected analyte in the spatially defined area of the well.

The steps 502 to 508 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for analysing fluorospot assays, the method comprising:
    (i) illuminating a well of an assay plate having a plurality of wells, with a plurality of excitation lights, wherein at a given time, the well of the assay plate is illuminated by only one excitation light;
    (ii) capturing at least one image of the well, in raw image format, for each of the plurality of excitation lights;
    (iii) generating a model of analyte release distribution in the well for each of the plurality of excitation lights, wherein the generation of the model of analyte release distribution in the well for a given excitation light comprises:
        (a) deconvolving the captured at least one image of the well for the given excitation light to estimate a pre-diffusion analyte distribution; and
        (b) detecting at least one potential analyte release site based on local maxima in the pre-diffusion analyte distribution; and
    (iv) for the plurality of excitation lights employed to illuminate the well of the assay plate, clustering a plurality of co-positioned fluorospots as a multiple secretion fluorospot, wherein the clustering is performed for all generated models of analyte release distribution, and wherein the clustering determines at least one multiple secretion fluorospot, wherein the method includes:
    generating the model of analyte release distribution in the well for each of the plurality of excitation lights comprises optimizing the pre-diffusion analyte distribution based on the detected at least one potential release site; and
    modifying the model of analyte release distribution in the well to analyse at least one fluorospot therein, wherein optimizing the pre-diffusion analyte distribution, based on the detected at least one potential analyte release site, is implemented iteratively at least once, and comprises employing at least one of: alternating direction methods, multiplicative update rules, forward-backward proximal gradient algorithms.

2. A method according to claim 1, wherein the plurality of excitation lights for illuminating the well of the assay plate depends on at least one fluorophore-detected analyte distributed across the well.

3. A method according to claim 1, wherein modifying the model of analyte release distribution in the well is based on at least one user-selectable parameter, wherein the at least one parameter is selected from a group comprising: fluorospot intensity, fluorospot size, estimated amount of analyte release, fluorospot colour, area of interest in the well.

4. A method according to claim 1, wherein modifying the model of analyte release distribution in the well is based on at least one user-selectable parameter, wherein the at least one parameter is selected from a group comprising: fluorospot intensity, fluorospot size, estimated amount of analyte release, fluorospot colour, area of interest in the well.

5. A method according to claim 1, wherein clustering the plurality of co-positioned fluorospots employs a distance-based hierarchical clustering algorithm.

6. A method according to claim 1, further comprising displaying a resultant model of analyte release distribution in the well, wherein the model of analyte release distribution, based on the detected at least one potential analyte release site, is implemented iteratively at least once, and comprises employing at least one of: alternating direction methods, multiplicative update rules, forward-backward proximal gradient algorithms, wherein the resultant model comprises the detected at least one fluorospot, and wherein single secretion fluorospots and multiple secretion fluorospots are represented.

7. A system for analysing fluorospot assays, the system comprising:
    (i) a light source arrangement configured to generate a plurality of excitation lights, wherein at a given time, the light source arrangement generates only one excitation light;
    (ii) a collimation arrangement positioned on an optical path of a generated excitation light, wherein the collimation arrangement is configured to collimate the generated excitation light;
    (iii) a multiband beam splitter positioned on an optical path of the collimated excitation light, the multiband beam splitter being supported by a support arrangement, wherein the multiband beam splitter is configured to:
        (a) reflect the collimated excitation light onto an assay plate for illuminating a well of the assay plate having a plurality of wells;
        (b) receive a reflection of the excitation light and an emitted light from the assay plate; and
        (c) reflect a portion of the reflected excitation light whilst transmitting a remaining portion of the reflected excitation light and the emitted light to a filtering arrangement;
    (iv) the filtering arrangement comprising a filter wheel and at least one emission filter, wherein the filter wheel is configured to accommodate the at least one emission filter therein, and wherein the at least one emission filter is configured to
        (d) remove the remaining portion of the reflected excitation light received from the multiband beam splitter; and
        (e) purify the emitted light whilst transmitting the emitted light to an optic arrangement;
    (v) the optical arrangement configured to direct the purified emitted light onto an imaging device;
    (vi) the imaging device configured to capture at least one image of the well, in raw image format, for each of the plurality of excitation light; and
    (vii) a processing module coupled to the imaging device, wherein the processing module is configured to
        (f) generate a model of analyte release distribution in the well for each of the plurality of excitation lights by optimizing a pre-diffusion analyte distribution based on the detected at least one potential release site; wherein optimizing the pre-diffusion analyte distribution is implemented iteratively at least once, and comprises employing at least one of: alternating direction methods, multiplicative update rules, forward-backward proximal gradient algorithms; and
        (g) for the plurality of excitation lights employed to illuminate the well of the assay plate, cluster a plurality of co-positioned fluorospots as a multiple secretion fluorospot, wherein the clustering is performed for all generated models of analyte release distribution, and wherein the clustering determines at least one multiple secretion fluorospot.

8. A system according to claim 7, wherein the system further comprises at least one excitation filter positioned on an optical path of the collimated excitation light, and wherein the at least one excitation filter is configured to purify the collimated excitation light.

9. A system according to claim 7, wherein the light source arrangement comprises at least one light source positioned on an actuator arrangement, wherein the at least one light source is implemented by way of at least one of: Light Emitting Diode, halogen light source, xenon light source, laser light source.

10. A system according to claim 7, wherein the multiband beam splitter is implemented by way of at least one of: a transparent mirror, a semi-transparent mirror, a prism, a dichroic mirror.

11. A system according to claim 7, wherein the optical arrangement comprises at least one of: telecentric lens, macro lens.

12. A system according to claim 7, wherein the support arrangement is a filter cube.

13. A system according to claim 7, further comprising a visualization module coupled to the imaging device and the processing module, wherein the visualization module comprises a user interface rendered on a computing device associated with a user, and wherein the visualization module is configured to perform at least of: display the captured at least one image for each of the at least one excitation light, display the generated model of analyte release distribution in the well for each of the at least one excitation light, receive user input to control operation of the processing module, display a resultant model of analyte release distribution in the well.

* * * * *